United States Patent
Stark et al.

(10) Patent No.: US 8,716,204 B2
(45) Date of Patent: May 6, 2014

(54) SYNTHETIC SYNOVIAL FLUID COMPOSITIONS AND METHODS FOR MAKING THE SAME

(75) Inventors: Norman Stark, Winterthur (CH); Maria S. Streckenbach, Immenstaad (DE); Seth Gilchrist, Vancouver (CH); Thorsten Schwenke, Winterthur (CH); Brian Thomas, Lakeland, FL (US)

(73) Assignee: Zimmer, Inc., Warsaw, IN (US)

( * ) Notice: Subject to any disclaimer, the term of this patent is extended or adjusted under 35 U.S.C. 154(b) by 169 days.

(21) Appl. No.: 13/191,193

(22) Filed: Jul. 26, 2011

(65) Prior Publication Data

US 2012/0186356 A1    Jul. 26, 2012

Related U.S. Application Data

(60) Provisional application No. 61/368,145, filed on Jul. 27, 2010.

(51) Int. Cl.
*C10M 169/06* (2006.01)
*G01N 3/56* (2006.01)

(52) U.S. Cl.
USPC ............... 508/163; 73/760; 73/10; 73/865.5

(58) Field of Classification Search
USPC ...................... 73/760, 10, 865.5; 508/163
See application file for complete search history.

(56) References Cited

U.S. PATENT DOCUMENTS

| | | | |
|---|---|---|---|
| 5,143,724 A | 9/1992 | Leshchiner et al. |
| 5,273,742 A | 12/1993 | Gould et al. |
| 5,399,351 A | 3/1995 | Leshchiner et al. |
| 5,515,590 A | 5/1996 | Pienkowski |
| 5,733,562 A | 3/1998 | Lee |
| 5,874,500 A | 2/1999 | Rhee et al. |
| 5,879,388 A | 3/1999 | Pienkowski et al. |
| 6,143,037 A | 11/2000 | Goldstein et al. |
| 6,262,127 B1 | 7/2001 | Acemoglu et al. |
| 6,635,267 B1 | 10/2003 | Miyoshi et al. |
| 6,656,459 B2 | 12/2003 | Kabanov et al. |
| 6,800,298 B1 | 10/2004 | Burdick et al. |
| 7,014,860 B1 | 3/2006 | Kawata et al. |
| 7,223,422 B2 | 5/2007 | Meader et al. |
| 7,374,774 B2 | 5/2008 | Bowlin et al. |

(Continued)

FOREIGN PATENT DOCUMENTS

| | | |
|---|---|---|
| CN | 103052394 A | 4/2013 |
| WO | WO 01/85179 A2 | 11/2001 |

(Continued)

OTHER PUBLICATIONS

Farfield Group. "Real Time, High Resolution Studies of Lipid Bilayer Formation" Application Note 006. [Online] Jan. 6, 2009. "http://web.archive.org/web/20090106042219/http://www.farfield-group.com/bio_ss.asp".*

(Continued)

*Primary Examiner* — Lisa Caputo
*Assistant Examiner* — Jonathan Dunlap
(74) *Attorney, Agent, or Firm* — Schwegman Lundberg & Woessner, P.A.

(57) ABSTRACT

Artificial or synthetic synovial fluids and methods for making such fluids are disclosed. The fluid includes selected proteins, phospholipids and hyaluronic acid and mimics the properties of human synovial fluid.

19 Claims, 2 Drawing Sheets

(56) References Cited

U.S. PATENT DOCUMENTS

| | | | |
|---|---|---|---|
| 7,459,307 | B2 | 12/2008 | Ha et al. |
| 7,547,453 | B2 | 6/2009 | Meader et al. |
| 7,658,950 | B2 | 2/2010 | Meader et al. |
| 7,731,981 | B2 | 6/2010 | Trieu et al. |
| 7,849,751 | B2 * | 12/2010 | Clark et al. ............ 73/768 |
| 2004/0142465 | A1 | 7/2004 | Radice et al. |
| 2005/0027069 | A1 | 2/2005 | Rhee et al. |
| 2005/0142152 | A1 | 6/2005 | Leshchiner et al. |
| 2005/0164981 | A1 | 7/2005 | Burdick et al. |
| 2006/0216324 | A1 | 9/2006 | Stucke et al. |
| 2007/0160680 | A1 | 7/2007 | Schwenke |
| 2007/0167397 | A1 | 7/2007 | Dillon et al. |
| 2007/0190083 | A1 | 8/2007 | Scifert et al. |
| 2007/0243218 | A1 | 10/2007 | Ellinghuysen et al. |
| 2007/0275030 | A1 | 11/2007 | Muratoglu et al. |
| 2008/0124370 | A1 | 5/2008 | Marx |
| 2008/0202252 | A1 | 8/2008 | Zubok et al. |
| 2008/0214417 | A1 | 9/2008 | Brandt et al. |
| 2008/0220044 | A1 * | 9/2008 | Semler et al. ............ 424/423 |
| 2008/0221064 | A1 * | 9/2008 | Ueno et al. ............ 514/54 |
| 2008/0287369 | A1 | 11/2008 | Jay |
| 2009/0004276 | A1 | 1/2009 | Ben-Shalom et al. |
| 2009/0010986 | A1 | 1/2009 | Ashton et al. |
| 2009/0060971 | A1 | 3/2009 | McKay |
| 2009/0117070 | A1 | 5/2009 | Daniloff et al. |
| 2009/0226499 | A1 | 9/2009 | Wisniewski et al. |
| 2010/0010159 | A1 | 1/2010 | Belcheva |
| 2010/0015196 | A1 | 1/2010 | Kimble et al. |
| 2010/0028399 | A1 | 2/2010 | Hornof |
| 2010/0048458 | A1 | 2/2010 | Jay |
| 2010/0074935 | A1 | 3/2010 | Flannery et al. |
| 2010/0080848 | A1 | 4/2010 | Flannery et al. |
| 2010/0098749 | A1 | 4/2010 | Barenholz et al. |
| 2010/0112014 | A1 | 5/2010 | Gilbert et al. |
| 2010/0143487 | A1 | 6/2010 | Masters |
| 2010/0174372 | A1 | 7/2010 | Kunze et al. |
| 2010/0189757 | A1 | 7/2010 | McKay |
| 2010/0284937 | A1 * | 11/2010 | Zhao et al. ............ 424/43 |
| 2012/0266699 | A1 * | 10/2012 | Brandt et al. ............ 73/865.6 |

FOREIGN PATENT DOCUMENTS

| | | |
|---|---|---|
| WO | WO 03/000191 A2 | 1/2003 |
| WO | WO 2005/079345 A2 | 9/2005 |
| WO | WO 2006/133711 A2 | 12/2006 |
| WO | WO 2007/019439 A2 | 2/2007 |
| WO | WO 2007/099307 A1 | 9/2007 |
| WO | WO 2008/038292 A2 | 4/2008 |
| WO | WO 2009/150651 A1 | 12/2009 |
| WO | WO 2010/009111 A2 | 1/2010 |
| WO | WO-2012013344 A1 | 2/2012 |

OTHER PUBLICATIONS

Nuki et al. "Rheological Simulation of Synovial Fluid by a Synthetic Polymer Solution" Nature 224, pp. 1118-1119. Dec. 13, 1969. "http://www.nature.com/nature/journal/v224/n5224/pdf/2241118a0.pdf".*

Sigma-Aldrich. "Phosphate Buffered Saline System" PBS1 Datasheet. Feb. 2009. "http://www.sigmaaldrich.com/etc/medialib/docs/Sigma/Datasheet/pbs1dat.Par.0001.File.tmp/pbs1dat.pdf".*

Liang, Jing. "Investigation of Synthetic and Natural Lubricants" Dissertation. Aug. 19, 2008. "http://repository.lib.ncsu.edu/ir/handle/1840.16/5805".*

"Plasma Osmolality" Wikipedia <http://en.wikipedia.org/wiki/Plasma_osmolality> Accessed Sep. 21, 2013.*

Erstad, Brian. "Osmolality and Osmolarity: Narrowing the Terminology Gap". Pharamcotherapy. 2003; 23(9). <http://www.medscape.com/viewarticle/461379>.*

Tidy, Colin, Dr. "Osmolality, Osmolarity and Fluid Homeostasis". Accessed Sep. 21, 2013. <http://www.patient.co.uk/doctor/osmolality-osmolarity-and-fluid-homeostasis>.*

Notification of Transmittal of International Search Report and Written Opinion for PCT/EP2011/003772 dated Oct. 19, 2011.

Hills, et al., "Surfactants identified in synovial fluid and their ability to act as boundary lubricants", Annals of the Rheumatic Diseases, vol. 43, pp. 641-648, 1984.

Blewis, et al., "A Model of Synovial Fluid Lubricant Composition in Normal and Injured Joints", European Cells and Materials, vol. 13, pp. 26-39, 2007.

Gardner, et al., "Living articular cartilage is not smooth", Annals of the Rheumatic Diseases, vol. 30, pp. 3-9, 1971.

Rwei, et al., "Viscoelasticity and wearability of hyaluronate solutions", Biochemical Engineering Journal, vol. 40, pp. 211-217, 2008.

Hills, B.A., "Remarkable Anti-Wear Properties of Joint Surfactant", Annals of Biomedical Enginnering, vol. 23 pp. 112-115, 1995.

Li, et al., "Lubricating Behaviour of Hyaluronic Acid in Artificial Articular Materials", English Abstract from Journal of University of Science and Technology Beijing, 2000.

Yu, et al., "Effects of the Addition of La-Dipalmitoyl Phosphatidylcholin and y-globulin on the Lubricating Behavior of Hyaluronic Acid", English Abstract from Journal of Univ. of Science & Technology Beijing, 2001.

Vadilenkaitis, et al., "Artificial synovial Fluid for the intra-articular treatment of rheumatoid arthritis and osteoarthritis (chemical synthesis and clinico-experimental and biomechanical data)", English Abstract from Ter Arkh, vol. 56 No. 11, 1984.

"International Application Serial No. PCT/EP2011/003772, International Preliminary Report on Patentability mailed Oct. 25, 2012", 14 pgs.

"International Application Serial No. PCT/EP2011/003772, Written Opinion mailed Jul. 20, 2012", 6 pgs.

Ferguson, J., et al., "Rheological simulation of synovial fluid by a synthetic macromolecular solution", Abstract from Rheologica Acta, vol. 10, No. 1, (Mar. 1971), 3 pgs.

Nuki, et al., "Rheological Simulation of Synovial Fluid by a Synthetic Polymer Solution", Abstract from Nature, vol. 224, (Dec. 13, 1969), 1118-1119.

* cited by examiner

SYNTHETIC SYNOVIAL FLUID COMPOSITIONS AND METHODS FOR MAKING THE SAME

RELATED APPLICATIONS

This application claims the benefit of and priority to U.S. Provisional Application Ser. No. 61/368,145, filed Jul. 27, 2010, the contents of which are incorporated by reference herein.

TECHNICAL FIELD

The present disclosure relates to artificial or synthetic lubricating fluids and to methods of making such fluids. More specifically, the present disclosure relates to artificial or synthetic lubricating fluids for use in the tribological testing of orthopedic implants.

BACKGROUND

Synovial fluid is a biological fluid that is found in the synovial cavity of the joints (e.g., knee, hip, shoulder) of the human body between the cartilage and synovium of facing articulating surfaces. Synovial fluid provides nourishment to the cartilage and also serves as a lubricant for the joints. The cells of the cartilage and synovium secrete fluid and the fluid lubricates and reduces friction between the articulating surfaces.

Human synovial fluid is comprised of approximately 85% water. It is derived from the dialysate of blood plasma, which itself is made up of water, dissolved proteins, glucose, clotting factors, mineral ions, hormones, etc. The proteins, albumin and globulins, are present in synovial fluid and are believed to play an important role in the lubrication of the joint area. Other proteins are also found in human synovial fluid, including the glycoproteins such as AGP, A1AT and lubricin.

Another compound that is present in human synovial fluid is hyaluronic acid. Hyaluronic acid is also believed to play a role in lubrication. Human synovial fluid further includes other compounds, such as polysaccharides and phospholipids. The phospholipid, dipalmitoylphosphatidylcholine (DPPC), is also present in human synovial fluid. DPPC is generally regarded as surfactant and is also believed to play a role in the lubrication of the joint.

With the increasing use of artificial orthopedic implants in the treatment of orthopedic injury and disease, the tribology of articulating surfaces in orthopedic implants has become an important area of study. As developers of artificial orthopedic implants attempt to prolong the useful life of orthopedic implants, understanding the amount and degree of wear and friction on the articulating surfaces when such devices are implanted in the body has generated ever-increasing interest among those in the orthopedic field. Accordingly, it is now appreciated that the role of synovial fluid in the tribology of the artificial orthopedic implants must be taken into account.

Testing of implants with human synovial fluid is not practical and may not be desirable for at least several reasons. First, there is simply not enough human synovial fluid available to supply those testing the orthopedic implants. Moreover, the composition of human synovial fluid is very patient specific and, therefore, highly variable. The characteristics of synovial fluid derived from humans may vary, and may be affected by such factors as joint physiology and the state of disease in the joint (if any). Thus, even if human synovial fluid were readily and abundantly available, the testing of orthopedic implants in such fluid would likely lead to variable results and potentially mask the results of any study using such fluid.

Thus, substitutes for human synovial fluid have been developed for studying the tribology of orthopedic implants. These substitutes have been developed to mimic or otherwise simulate the properties and characteristics of human synovial fluid when such fluid is in contact with materials commonly used for orthopedic implants such as, but not limited to, ultrahigh molecular weight polyethylene (UHMWPE) and cobalt-chrome.

Certain early substitutes for synovial fluid were based on water and/or a saline solution, such as the well known Ringers solution. However, these solutions did not adequately simulate or behave like human synovial fluid and often resulted in non-physiological wear rates and patterns. Accordingly, other lubricants believed to more closely approximate the properties of human synovial fluid have been developed.

Bovine serum and solutions based on bovine serum have commonly been used as a substitute for human synovial fluid in tribological testing. The bovine serum can either be normal bovine serum, bovine calf serum and/or fetal bovine serum. The bovine serum is often mixed with water and other components, such as buffers and antibiotics. For example, U.S. Patent Application Publication No. 2007/0160680 discloses an artificial lubricant that includes bovine calf serum. The lubricant further includes additives such as hyaluronic acid and phospholipids of the type naturally found in synovial fluid. In addition, antibiotics, a chelating agent and buffers are also included in the artificial lubricant disclosed therein.

U.S. Patent Application Publication No. 2008/0214417 discloses studies that were conducted with an artificial synovial fluid based on bovine calf serum, newborn calf serum and alpha calf serum. Other studies involving the use of bovine serum as an artificial synovial fluid are reported in the non-patent literature, as are studies of other formulations devoid of bovine serum or the constituents thereof. See Ahlroos T., Saikko, V.; "Wear of Prosthetic Joint Materials in Various Lubricants," Wear, 211(1): 113-119, 1997.

Whether bovine serum adequately mimics human synovial fluid is not, however, without debate. One question that has been raised is whether current bovine serum based lubricants adequately resemble the human synovial fluid when one considers the components that are believed to contribute to lubrication. For example, the ratio of proteins found in human synovial fluid may not be adequately represented by the synthetic lubricants that are based on bovine serum alone. Moreover, inclusion of bovine serum as a whole introduces additional variables which may not be desirable and may skew the results of any tribological testing.

Thus, there continues to be a need for an artificial lubricant that is more similar to human synovial fluid in its composition, including, but not limited to, protein content and protein ratio, and also in certain of its properties, including (but not limited to) its non-newtonian characteristics. There is also a need for an artificial synovial fluid that remains stable for an extended period of time and does not undergo rapid degradation. In addition, there exists a need for an artificial synovial fluid that is reproducible and eliminates the variables that are introduced by some of the current synthetic synovial fluid lubricants.

SUMMARY

There are several aspects to the compositions and methods disclosed herein.

In a first aspect, the present disclosure is directed to a synthetic fluid composition comprising about 6-18 mg/ml of albumin, about 4-12 mg/ml of gamma-globulin, about 0.04-0.1 mg/ml of phospholipid, and about 2-4 mg/ml of hyaluronic acid in a phosphate buffered saline solution. The composition has a pH of about 7.0-7.4 mg/ml and an osmolality of about 280-320 mOssm/kg.

In another aspect, the present disclosure is directed to a synthetic fluid composition that mimics selected properties of human synovial fluid. The composition includes about 6-18 mg/ml of albumin, about 4-12 mg/ml of gamma-globulin, about 0.04-0.1 mg/ml of phospholipid, and about 2-4 mg/ml of hyaluronic acid in a phosphate buffered saline solution. The composition has a pH of about 7.0-7.4 mg/ml and an osmolality of about 280-320 mOsm/kg.

In a further aspect, the present disclosure is directed to a method of preparing a synthetic synovial fluid. The method includes adding about 0.04-0.1 mg/ml of a phospholipid to a phosphate buffered saline to form a suspension. The method further includes agitating the suspension for a selected period of time and then adding about 2-4 mg/ml of hyaluronic acid to the suspension and mixing the same to dissolve the hyaluronic acid in the suspension. Further, 6-18 mg/ml of albumin are added, mixed, and dissolved in the suspension. The method also includes adding 4-12 mg/ml of gamma-globulin to the suspension and agitating the same to dissolve the gamma-globulin in the suspension.

In yet another aspect, the present disclosure is directed to a method for testing the wear on an orthopedic implant. This method includes providing an orthopedic implant sample having at least one pair of facing articulating surfaces. The method includes introducing a synthetic fluid composition between the articulating surfaces. The composition includes a phosphate buffered saline with about 6-18 mg/ml of albumin, about 4-12 mg/ml of gamma-globulin, about 0.04-0.1 mg/ml of a phospholipid, and about 2-4 mg/ml of hyaluronic acid. The composition has a pH of about 7.0-7.4 and an osmolality of about 280-320 mOsm/kg. The method further includes causing one of said articulating surfaces to move relative to the other articulating surface.

In a more specific aspect, the present disclosure is directed to a synthetic fluid composition comprising about 12 mg/ml albumin, about 7 mg/ml gamma-globulin, about 0.1 mg/ml dipalmitoylphosphatidylcholine, and about 2 mg/ml hyaluronic acid, all in a phosphate buffered saline solution. The composition has a pH of about 7.1 and an osmolality of about 297 mOsm/kg.

In another aspect, the present disclosure is directed to a synthetic fluid composition that consists essentially of albumin, gamma-globulin, dipalmitoylphosphatidylcholine, and hyaluronic acid in a phosphate buffered saline solution.

DETAILED DESCRIPTION

Figure 1:
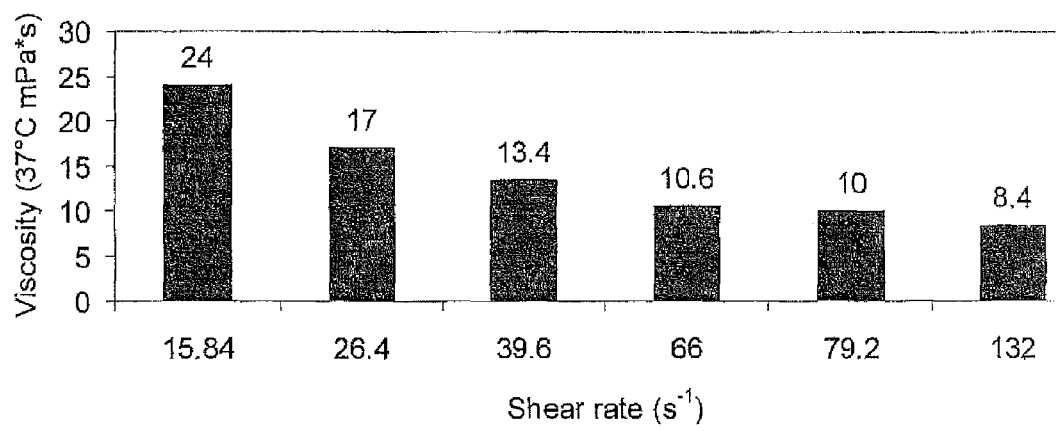
FIG. 1 is a graph showing the non-newtonian properties of the artificial synovial fluid described herein.

Disclosed herein are synthetic or artificial lubricating fluids useful in the wear/friction testing of orthopedic implants and in orthopedic implant tribological testing generally. As used herein, the term "synthetic" or "artificial" solution refers to a solution that is not wholly or entirely derived from humans or other mammals, even if some of the solution's constituents are derived from humans or other mammals. Thus, a synthetic solution or artificial solution may include a solution where one or more constituents are made by and/or derived from the body of a human or mammal, while the solution as a whole is formulated outside of the body of a human or mammal. In the context of the fluids described and claimed herein, synthetic fluids or artificial fluids may include certain proteins (such as albumin or gamma-globulins) or other constituents derived from, for example, human synovial fluid, blood serum, bovine serum, bovine blood and the like. However, they do not include bovine or other mammalian serum, as a whole, as a constituent of the artificial synovial fluid.

The synthetic or artificial fluids disclosed herein exhibit or possess properties that simulate or mimic selected properties of human synovial fluid. For example, the synthetic fluids disclosed herein and described below may be non-newtonian, as is human synovial fluid. In addition, the synthetic synovial fluids described herein may have a protein content that is similar to the protein content found in human synovial fluid. Finally, the synthetic synovial fluids described herein may include a protein ratio that is similar to the protein ratio (for example, the ratio of albumin to gamma-globulins) found in human synovial fluid. The synthetic or artificial synovial fluids described herein also have an enhanced stability and are, therefore, less prone to degradation over extended time periods. Moreover, the synthetic synovial fluids described herein are reproducible and are generally subject to fewer variables than the synthetic synovial fluids currently in use, including those that are based on, derived from, or substantially comprise bovine serum.

The synthetic synovial fluid composition described herein includes a starting solution in which several other components are dissolved. In one embodiment, the starting solution is a buffered electrolytic solution having a pH of at least 7.0. In another embodiment, the starting solution has a pH between about 7.0 and 7.4. In a more specific embodiment, the starting solution is a phosphate buffered saline. Phosphate buffered saline (PBS) is a known solution that includes approximately 137 mM sodium chloride (NaCl), about 2.7 mM potassium chloride (KCl), 10 mM sodium phosphate dibasic ($Na_2HPO_4$), 2 mM potassium phosphate monobasic ($KH_2PO_4$) with a pH of approximately 7.4. Other solutions may also be used as the starting solution for the synthetic synovial fluid described herein. For example, a Ringers solution or a modified Ringers solution may also be used. Ringers solution is an electrolytic solution and includes some of the components of the constituents of the PBS described above with the exception of the buffer. Thus, a buffer can be added to Ringers or a Ringers-type solution to provide a starting solution.

The synthetic synovial fluid described herein also includes proteins and specifically includes certain selected proteins that are present in human synovial fluid. Thus, the synthetic synovial fluid may include albumin and one or more of the globulins commonly found in human synovial fluid. In particular, albumin and gamma-globulin are included in the synthetic synovial fluid of the present disclosure and may be derived from bovine serum, bovine blood or other available mammalian sources. While these proteins may be derived from, for example, bovine serum, the bovine serum as a whole is not included in the synthetic synovial fluid disclosed herein.

As discussed above, protein concentrations and protein ratios in bovine serum differ from those found in human synovial fluid. Moreover, bovine serum as a whole may introduce variables which are not desirable and cannot be controlled. Thus, in accordance with the synthetic synovial fluid described herein, certain selected protein constituents found in bovine serum (or other mammalian serum) are included. This allows for a more controlled composition and one that can be tailored to more closely resemble the protein content and ratio of human synovial fluid and simulate human synovial fluid generally.

In one embodiment, the total protein content in the synthetic synovial fluid composition described herein may be about 10-30 mg/ml. More preferably, the total protein content may be about 15-25 mg/ml with about 18 mg/ml being more preferred.

In addition to the total protein content, the synthetic synovial fluid described herein preferably includes a protein ratio that is similar to the protein ratio, i.e., albumin to gamma-globulin, typically found in human synovial fluid. The ratio of albumin to gamma-globulin in human synovial fluid has been reported to be between approximately 1.7:1 and 2.3:1. Similarly, the ratio of albumin to gamma-globulins in the synthetic synovial fluid of the present disclosure will be between about approximately 1.5:1 and 2.5:1 with a preferred ratio of approximately 1.7:1 albumin to globulin.

With respect to the individual proteins, the concentration of albumin in the synthetic synovial fluid composition of the present disclosure is preferably about 6-18 mg/ml. More specifically, the concentration of albumin may be about 10-14 mg/ml with about 12 mg/ml being more preferred. With respect to the gamma-globulin proteins, these may be present in the synthetic synovial fluid composition in a concentration of about 4-12 mg/ml or more preferably 6-8 mg/ml with about 7 mg/ml being most preferred.

As discussed above, human synovial fluid also naturally includes phospholipids which are known surfactants and are also believed to contribute to lubrication. Accordingly, the synthetic synovial fluid composition of the present disclosure may include a selected concentration of one or more phospholipids. In one embodiment, the synthetic synovial fluid composition includes dipalmitoylphosphatidylcholine (DPPC). The concentration of the DPPC in the synthetic synovial fluid composition may be about 0.04-0.15 mg/ml and more preferably about 0.08-0.12 mg/ml. A concentration of approximately 0.1 mg/ml may be more preferred.

Another constituent of the synthetic synovial fluid composition of the present disclosure that also has a lubricating effect is hyaluronic acid. Hyaluronic acid is included in the formulation of the synthetic synovial fluid in a concentration of about 1-4 mg/ml with about 2 mg/ml being more preferred.

Accordingly, in one embodiment, the synthetic synovial fluid composition includes about 6-18 mg/ml of albumin; about 4-12 mg/ml of gamma-globulin; about 0.04-0.15 mg/ml of DPPC and between about 1-4 mg/ml of hyaluronic acid, in a phosphate buffered saline, with a pH of approximately 7.0-7.4 and a osmolality of about 280-320 mOsm/kg.

In a more specific embodiment, the synthetic synovial fluid described herein includes about 12 mg/ml of albumin; about 7 mg/ml of gamma-globulin; about 0.1 mg/ml of DPPC and about 2 mg/ml hyaluronic acid, in a phosphate buffered saline with a pH of approximately 7.1 and an osmolality of about 297 mOsm/kg. The composition is considered stable in that it maintains pH (of approximately 7.1) for up to at least 90 days.

Of course, it will be appreciated that other additives may be included in the composition of the present disclosure. However, in one embodiment, no other additives are added including other constituents that are typically found in bovine serum or human or bovine synovial fluid such as, for example, alpha 1 globulin, alpha 2 globulin or beta globulin. Thus, in one embodiment, the artificial synovial fluid composition of the present disclosure consists essentially of albumin, gamma globulin, DPPC and hyaluronic acid in a phosphate buffered saline.

The preparation of phosphate buffered saline solution is well known in the art and will not be discussed in detail here. Typically, a tablet of the phosphate buffered saline is dissolved in an amount of distilled water. Such tablets are formulated to give a ready-to-use PBS solution upon dissolution in a specified quantity of distilled water. Tablets are available in the standard volumes (e.g., 100 ml, 500 ml, 1,000 ml).

Once the PBS solution has been prepared, the phospholipid, typically DPPC, is added to the PBS solution to arrive at the desired concentration as described above. The DPPC/PBS suspension is then subjected to agitation in order to disperse the phospholipid in the PBS. Typically, the suspension will be subjected to an ultrasonic bath for a selected period of time to allow the phospholipids to disperse and form micelles. A typical length for the ultrasonic bath treatment is between 10 to 30 minutes. However, the time may be prolonged if the particles are not adequately dispersed.

After adequate agitation (by, for example, sonication), the resulting suspension is then removed from the sonicator and the remaining constituents may be added. It is preferred to mix the remaining constituents by stirring (such as on a stir plate), or by an alternative form of agitation other than sonication, as sonication may result in degradation of the remaining components. Accordingly, an amount of hyaluronic acid is added and dissolved in the suspension. Albumin is also added and stirred until dissolved and no particles are visible. Finally, a selected amount of gamma-globulin is added and stirred until it is dissolved and no particles are visible. The amounts of the hyaluronic acid, albumin, and gamma-globulin are selected to arrive at the concentrations for such constituents described above. While the order of mixing and stirring the remaining constituents described above is preferred, the hyaluronic acid, albumin and gamma-globulin may be added in any order.

As discussed above, the synthetic synovial fluid compositions described herein are useful in the testing of wear and friction and general tribology of the orthopedic implants commonly used in the medical field. Such testing is commonplace in the orthopedic implant industry and details of the methodology and apparatus used for such testing will not be described here. Typically, a reciprocating apparatus is used to mimic movement of the joint and thereby measure the friction and wear of the orthopedic implant. The reciprocating movement causes the articulating surfaces to move relative to one another. This step is repeated for several and typically many cycles.

The synthetic synovial fluid described herein has properties that are comparable to that of human synovial fluid. For example, the synthetic synovial fluid displays non-newtonian characteristics much like human synovial fluid. In one example, the viscosity of the synthetic synovial fluid described herein was measured at different shear rates at 37°. The size of the sample was about 100 ml. The Brookfield LV-DV-1 Plus Rotational Viscosimeter with spindle 18 was used. FIG. 1 shows the resulting values and the non-newtonian behavior of the synthetic synovial fluid which included approximately 12 mg/ml of albumin, 7 mg/ml of gamma-globulins, 0.1 mg/ml of DPPC and 2 mg/ml of hyaluronic acid in a phosphate buffered saline; pH of approximately 7.1 and osmolality of about 297 mOsm/kg. As shown in FIG. 1, as shear rate increases, the viscosity of the resulting synthetic synovial fluid was reduced.

Study

Figure 2:
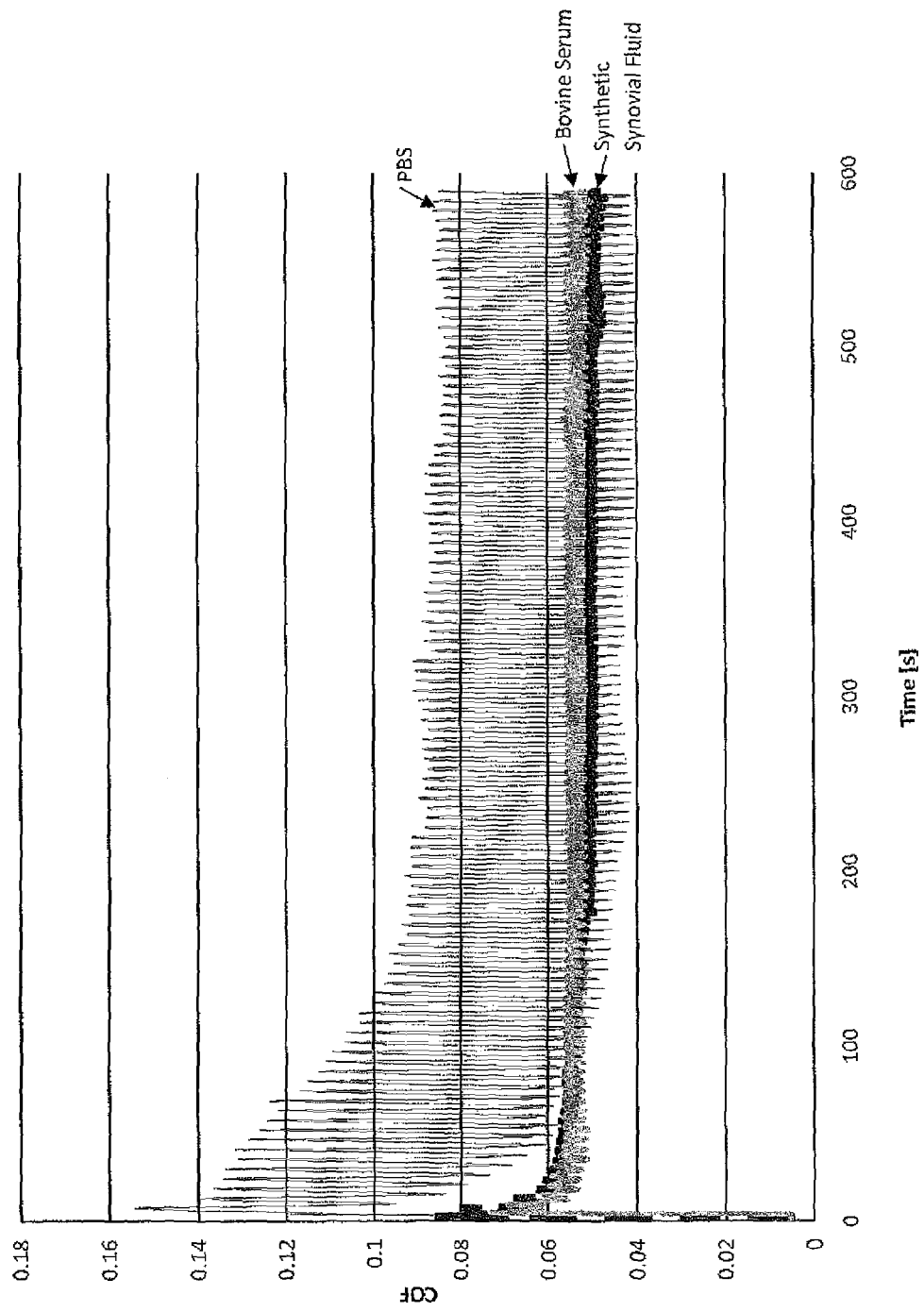
FIG. 2 is a graph showing the pin on disk (POD) test results comparing Coefficients of Friction (COF) over time of ultra high molecular weight polyethylene (UHMWPE) pins on cobalt-chrome (CoCr) disks in (a) phosphate buffered saline, (b) bovine serum, and (c) synthetic synovial fluid as described herein.

In a study, the lubricating properties of three (3) fluids were analyzed and compared. The study was conducted in general accordance with ASTM G99-05. The fluids used were phosphate buffered saline (PBS) available from Sigma-Aldrich, bovine serum available from Hyclone, and the synthetic synovial fluid described herein which included approximately: 12 mg/ml of albumin, 7 mg/ml of gamma-globulins, 0.1 mg/ml of DPPC and 2 mg/ml of hyaluronic acid in a phosphate buffered saline; pH of approximately 7.1 and osmolality of about 297 mOsm/kg. A custom modified pin-on-rotating-disk device (LSRH-Tribometer, Pin-Disc Machine, Serial No. 3-108; CSM Instruments SA, Peseux, Switzerland) was equipped with an ultra high molecular weight polyethylene (UHMWPE) pin articulating against a cobalt-chrome (CoCr) disk. The respective specimen chamber(s) were filled with one of the three (3) lubricating fluids identified above so that the pin-disk contact was completely submersed. A greater amplitude in the recorded signals indicated increased "stick and slip" behavior of the UHMWPE and CoCr components in a given lubricating liquid. As shown in FIG. 2, of the three (3) fluids tested, the synthetic synovial fluid was the most stable.

It will be understood that the embodiments described above are illustrative of some of the applications of the principles of the present subject matter. It will also be understood that certain modifications may be made by those skilled in the art without departing from the spirit and scope of the claimed subject matter, including those combinations of features that are individually disclosed or claimed herein. For all of these reasons, the scope of the invention is not limited to the above description but is as set forth in the following claims, and it will be understood that the claims may be directed to the features including a combinations of features that are individually disclosed or claimed herein.

The invention claimed is:

1. A synthetic fluid composition comprising:
    a) about 6-18 mg/ml of albumin;
    b) about 4-12 mg/ml of gamma-globulin, wherein the ratio of albumin to gamma-globulin is between 1.7:1 and 2.3:1;
    c) 0.04-0.1 mg/ml of a phospholipid;
    d) about 2-4 mg/ml of hyaluronic acid;
    e) in a phosphate buffered saline solution, said composition having a pH of about 7.0-7.4 and an osmolality of about 280-320 mOsm/kg, wherein the synthetic fluid composition is free of bovine or other mammalian serum, as a whole, as a constituent of the synthetic fluid.

2. The fluid composition of claim 1 comprising about 12 mg/ml of albumin.

3. The fluid composition of claim 1 comprising about 7 mg/ml of gamma-globulin.

4. The fluid composition of claim 1 comprising 0.1 mg/ml of said phospholipid.

5. The fluid composition of claim 4 wherein said phospholipid comprises dipalmitoylphosphatidylcholine.

6. The fluid composition of claim 1 comprising about 2 mg/ml of hyaluronic acid.

7. The fluid composition of claim 1 wherein said pH is maintained at about 7.1 for at least 90 days.

8. The fluid composition of claim 1 wherein said fluid is a non-newtonian fluid.

9. The fluid composition of claim 8 wherein the viscosity of said fluid composition decreases at increasing shear rates at about 37° C.

10. The fluid composition of claim 1 wherein the total albumin and gamma-globulin concentration is about 10-30 mg/ml.

11. A synthetic fluid composition consisting essentially of albumin, gamma-globulin, dipalmitoylphosphatidylcholine and hyaluronic acid in a phosphate buffered saline solution.

12. The synthetic fluid composition of claim 1, wherein the synthetic fluid composition mimies selected properties of human synovial fluid.

13. A method of preparing a synthetic synovial fluid comprising:
    a) adding about to phosphate buffered saline to form a suspension;
    b) agitating said suspension for a selected period of time;
    c) adding hyaluronic acid to said suspension and mixing the same to dissolve said hyaluronic acid in said suspension;
    d) adding albumin and mixing the same to dissolve said albumin in said suspension; and
    e) adding gamma-globulin and mixing the same to dissolve said gamma-globulin in said suspension, such that a synthetic fluid composition comprising about 6-18 mg/ml of albumin, about 4-12 mg/ml of gamma-globulin, 0.04-0.1 mg/ml of phospholipid, and about 2-4mg/ml of hyaluronic acid is formed, said composition having a pH of about 7.0-7.4 and an osmolaity of about 280-320 mOsm/kg, wherein the ratio of albumin to gamma-globulin is between 1.7:1 and 2.3:1;
    wherein the synthetic fluid composition is free of bovine or other mammalian serum, as a whole, as a constituent of the synthetic fluid.

14. The method of claim 13 comprising agitating said suspension of phospholipid in said phosphate buffered saline in an ultrasonic bath.

15. The method of claim 14 wherein said suspension is agitated in said ultrasonic bath for about 10-30 minutes.

16. The method of claim 13 wherein said phosphlolipid comprises dipalmitoylphosphatidylcholine.

17. A method for testing the wear on an orthopedic implant comprising:
    a) providing an orthopedic implant sample having at least one pair of facing articulating surfaces;
    b) introducing a synthetic fluid composition between said articulating surfaces, said composition comprising:
        i. phosphate buffered saline with
        ii. about 6-18 mg/ml of albumin;
        iii. about 4-12 mg/ml of gamma-globulin, wherein the ratio of albumin to gamma-globulin is between 1.7:1 and 2.3:1;
        iv. 0.04-0.1 mg/ml of a phospholipid;
        v. about 2-4 mg/ml of hyaluronic acid; and
        vi. said composition having a pH of about 7.0-7.4 and an osmolality of about 280-320mOsm/kg; wherein the synthetic fluid composition is free of bovine or other mammalian serum, as a whole, as a constituent of the synthetic fluid;
    c) causing at least one of said articulating surfaces to move relative to said other articulating surface.

18. A fluid composition comprising:
    a) about 12 mg/ml of albumin;
    b) about 7 mg/ml of gamma-globulin, wherein the ratio of albumin to gamma-globulin is between 1.7:1 and 2.3:1;
    c) 0.1 mg/ml of dipalmitoylphosphatidylcholine;
    d) about 2 mg/ml of hyaluronic acid;

e) in a phosphate buffered saline, said composition having a pH of about 7.1 and an osmolality of about 297 mOsm/kg, wherein the synthetic fluid composition is free of bovine or other mammalian serum, as a whole, as a constituent of the synthetic fluid.

19. A synthetic fluid composition comprising:
a) about 6-18 mg/ml of albumin;
b) about 4-12 mg/ml of gamma-globulin;
c) 00.4-0.1 mg/ml of phospholipid;
d) 2-4 mg/ml of hyaluronic acid;
e) in a phosphate buffered saline solution, said composition having a pH of about 7.0-7.4 and an osmolality of about 280-320 mOsm/kg;
wherein the ratio of albumin to gamma-globulin is between 1.7:1 and 2.3:1, wherein the synthetic fluid composition is free of bovine or other mammalian serum, as a whole, as a constituent of the synthetic fluid.

* * * * *

UNITED STATES PATENT AND TRADEMARK OFFICE
CERTIFICATE OF CORRECTION

PATENT NO. : 8,716,204 B2  
APPLICATION NO. : 13/191193  
DATED : May 6, 2014  
INVENTOR(S) : Stark et al.

Page 1 of 1

It is certified that error appears in the above-identified patent and that said Letters Patent is hereby corrected as shown below:

On title page 2, in column 2, References Cited under "Other Publications", line 12, delete "Pharamcotherapy." and insert --Pharmacotherapy.--, therefor On title page 2, in column 2, References Cited under "Other Publications", line 35, delete "Phosphatidylcholin and y-globulin" and insert --Phosphatidylcholine and γ-globulin--, therefor In the Claims Column 8, line 1, in Claim 9, delete "8" and insert --1--, therefor Column 8, line 7, in Claim 11, delete "A" and insert --The--, therefor Column 8, line 7, in Claim 11, after "composition", insert --of claim 1,--, therefor Column 8, line 11, in Claim 12, delete "mimies" and insert --mimics--, therefor Column 8, line 15, in Claim 13, delete "about" and insert --a phospholipid--, therefor Column 8, line 29, in Claim 13, delete "osmolaity" and insert --osmolality--, therefor Column 8, line 56, in Claim 17, delete "kg;" and insert --kg,--, therefor Column 9, line 9, in Claim 19, delete "00.4-0.1" and insert --0.04-0.1--, therefor Column 9, line 9, in Claim 19, after "of", insert --a--, therefor Column 9, line 12, in Claim 19, delete "7.0-7.4and" and insert --7.0-7.4 and--, therefor Signed and Sealed this  
Twenty-fifth Day of November, 2014

Michelle K. Lee  
*Deputy Director of the United States Patent and Trademark Office*